(12) United States Patent
Lal (10) Patent No.: US 7,129,368 B2
(45) Date of Patent: Oct. 31, 2006

(54) PLATINUM CARBOXYLATE ANTICANCER COMPOUNDS

(75) Inventor: Manjari Lal, Redmond, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 0 days.

(21) Appl. No.: 11/080,348

(22) Filed: Mar. 14, 2005

(65) Prior Publication Data

US 2005/0209321 A1  Sep. 22, 2005

Related U.S. Application Data

(60) Provisional application No. 60/659,932, filed on Mar. 10, 2005, provisional application No. 60/553,108, filed on Mar. 15, 2004.

(51) Int. Cl.
*C07F 15/00* (2006.01)
*A61K 31/28* (2006.01)

(52) U.S. Cl. ...................... 556/137; 514/492

(58) Field of Classification Search ............... 556/137; 514/492
See application file for complete search history.

(56) References Cited

U.S. PATENT DOCUMENTS

| | | | |
|---|---|---|---|
| 4,140,707 A | 2/1979 | Cleare et al. | |
| 4,177,263 A | 12/1979 | Rosenberg et al. | |
| 4,533,502 A * | 8/1985 | Rochon et al. | 546/8 |
| 4,704,464 A | 11/1987 | Brunner et al. | |
| 5,117,022 A | 5/1992 | Khokhar et al. | |
| 5,648,384 A | 7/1997 | Kidani et al. | |
| 5,922,689 A | 7/1999 | Shaw | |
| 6,001,817 A | 12/1999 | Shaw | |
| 6,011,166 A | 1/2000 | Valsecchi et al. | |
| 6,130,345 A | 10/2000 | Doppelt | |
| 6,194,403 B1 | 2/2001 | Hu et al. | |
| 6,297,245 B1 | 10/2001 | Shaw | |
| 6,331,559 B1 | 12/2001 | Bingham et al. | |

FOREIGN PATENT DOCUMENTS

| | | |
|---|---|---|
| BE | 898 614 A1 | 5/1984 |
| GB | 2 019 397 A | 10/1979 |
| GB | 2 137 198 A | 10/1984 |
| WO | WO 96/16068 A1 | 5/1996 |
| WO | WO 00/63219 A1 | 10/2000 |

OTHER PUBLICATIONS

Kortes et al., Crystal and Molecular Structure of a Potentail DNA Groove-Spanning Chelate: [MV][Pt2(hdta)Cl2].4H2O (MV2+=1,1'-Dimethyl-4,4'-bipyridinium, hdta4-=1,6-Hexanediamine-N,N,N',N'-tetraacetate), Inorganic Chemistry, vol. 38, No. 22, pp. 5045-5052 (1999).*

Brunner, H., et al., "Porphyrin Platinum Conjugates—New Aims," *Inorganica Chimica Acta* 357:1649-1669, 2004.

Craciunescu, D., and A.D. Lopez, "Relation Between Structure and Antineoplastic Activity of New Cis-Pt$^{II}$(L)$_2$(X) and Pt$^{IV}$ (L)$_2$(OH)$_2$(X) Complexes, Where L-Cyclohexylamine and X$^{2-}$ Is the Dianion of an Organic Acid," *Anales De La Real Academia De Farmacia* 50(3):389-403, 1984.

(Continued)

Primary Examiner—Porfirio Nazario-Gonzalez
(74) Attorney, Agent, or Firm—Christensen, O'Connor Johnson Kindness PLLC (57) ABSTRACT

Platinum carboxylate anticancer compounds, pharmaceutical compositions that include the platinum carboxylate compounds, and methods for treating cellular proliferative diseases by administering the platinum carboxylate compounds.

23 Claims, 1 Drawing Sheet

OTHER PUBLICATIONS

Rochon, F.D., and P.-C. Kong, "Antitumor Evaluation of Some New Platinum Compounds," *Journal of Cinical Hematology and Oncology* 12(2):39-43, 1982.

Appleton, T.G., et al., "Amino Acid Complexes of Platinum(IV). VI. Ethylenediamine-tetraacetate (EDTA) Complexes," *Inorgica Chimica Acta*, 61:51-56, 1982.

Charalabopoulos, K., et al., "Antitumour and Toxic Effects on Wistar Rats of Two New Platinum Complexes," *European J. of Clin. Invest.* 32:129-133, 2002.

Criado, J.J., "Synthesis and Characterization of Sodium *cis*-dichlorochenodeoxycholylglycinato(O,N) Platinum(II)—Cytostatic Activity," *BioMetals* 12:281-288, 1999.

Fan, D., et al., "Antitumor Activity Against Human Tumor Samples of *cis*-Diamminedichloroplatinum(II) and Analogues of Equivalent *in Vitro* Myelotoxic Concentrations," *Cancer Research* 48:3135-3139, Jun. 1, 1988.

Galanski, M., "The Mode of Action of Antitumor Platinum Compounds Linked to Amino Phosphonic Acids With Particular Activity Against Bone Malignancies and the Influence of Calcium Ions Onto the DNA Binding Behavior," *Contrib Oncol.* 54:435-438, 1999.

Han, I., et al., "Enhanced Antitumor Activity of *trans*(±)-1,2-Diaminocyclo-hexaneglutamatoplatinum(II) Formulated With Stealth Liposome," *Biorgan & Medicinal Chem* 11:5443-5447, 2003.

Herrera, M.C., et al., "Comparison of the Effects of Bischolylglycinatechloro-Platinum(II) Versus Cisplatin on Liver Regeneration After Partial Hepatectomy," *Anticancer Res.* 18:3555-3564, 1998.

Jolley, J.N., et al., "Synthesis and Antitumour Activity of Platinum (II) and Platinum (IV) Complexes and Containing Ethylenediamine-Derived Ligands Having Alcohol, Carboxylic Acid and Acetate Substituents. Crystal and Molecular Structure of [PtL$^4$Cl$_2$] H$_2$O where L$^4$ is Ethylenediamine-N,N'-Diacetate," *J. Inorg. Biochem.* 83:91-100, 2001.

Kortes, R.A., "Crystal and Molecular Structure of a Potential DNA Grove-Spanning Chelate: [MV][Pt$_2$(hdta) Cl$_2$] 4H$_2$O (MV$^{2+}$=1, 1'-Dimethyl-4-4'-bipyridinium, hdta$^{4-}$=1,6-Hexanediamine-N,N,N'N'-tetraacetate)," *Inorg. Chem.* 38(22):5045-5052, Oct. 2, 1999.

Lautersztain, J., et al., "Antitumor Activity of Liposomal *Cis-Bis* N-Decyl-Iminodiacetato-1, 1-Diaminocyclohexane-Platinum (II) Against L1210 Leukemia and Metastases of M5076 Murine Reticulosarcoma," *J. Liposome Res.* 1(1):1-13, 1988-89.

Lin, F.-T., et al., "Substitution of Inosine for Chloride in [Pt$_2$(hdta)Cl$_2$]$^{2-}$(hdta$^{4-}$=1,6-hexanediamine-N,N,N',N'-tetraacetate)," *Inorganica Chimica Acta* 2:124-128, 1998.

Offiong, O.E., et al., "Synthesis, Spectral and Cytotoxicity Studies of Palladium(II) and Platinum(II) Amino Acid Schiff Base Complexes," *Trans. Metal. Chem.* 25:369-373, 2000.

Sandman, K.E., et al., "A Mechanism-Based, Solution-Phase Method for Screening Combinatorial Mixtures of Potential Platinum Anticancer Drugs," *JBIC* 3:74-80, 1998.

Sep. 17, 2003 Abstract, Derwent Publications Ltd., London, GB.

Akerley, W., et al., "Weekly, High-Dose Paclitaxel in Advanced Lung Carcinoma," *Cancer* 97(10):2480-2486, May 15, 2003.

Baumgartner, M.R., et al. "The Interaction of Transition Metals With the Coenzyme α-Lipoic Acid: Synthesis, Structure and Characterization of Copper and Zinc Complexes," *Inorganica Chimica Acta* 252:319-331, Nov. 1996.

Farrell, N., "Polynuclear Charged Platinum Compounds as a New Class of Anticancer Agents," in L.R. Kelland and N. Farrell (eds.), *Platinum-Based Drugs in Cancer Therapy*, Humana Press Inc., Totowa, New Jersey, Jun. 2000, pp. 321-339.

Fuertes, M.A., et al., "Novel Concepts in the Development of Platinum Antitumor Drugs," *Curr. Med. Chem.—Anti-Cancer Agents* 2(4):539-551, 2002.

Hegmans A., et al., "Novel Approaches to Polynuclear Platinum Pro-Drugs. Selective Release of Cytotoxic Platinum-Spermidine Species Through Hydrolytic Cleavage of Carbamates," *Inorg. Chem.* 40(24):6108-6114, Oct. 20, 2001.

Leonetti, C., et al., "α-Tocopherol Protects Against Cisplatin-Induced Toxicity Without Interfering With Antitumor Efficacy," *Int. J. Cancer* 104(2):243,250, 2003.

Manzotti, C., et al., "BBR 3464: A Novel Triplatinum Complex, Exhibiting a Preclinical Profile of Antitumor Efficacy Different from Cisplatin," *Clinical Cancer Res.* 6:2626-2634, Jul. 2000.

Martin-Ramos, J.D., et al., "Copper(II) and Nickel(II) Chelated With Dihydrogen Trans-1,2-Diaminocyclohexane-N,N,N'N'-Tetraacetate(2-) Ion (H$_2$CDTA$^{2-}$). Synthesis, XRD Structure and Properties of [Cu(H$_2$CDTA)] H$_2$O and [Ni(H$_2$CDTA)(H$_2$O)] 4H$_2$O", *Polyhedron* 15(3)439-446, 1996.

Pace, A., et al., "Neuroprotective Effect of Vitamin E Supplementation in Patients Treated With Cisplatin Chemotherapy," *J. Clin. Oncol.* 21(5):927-391 Mar. 2003.

Qu, Y., et al., "Synthesis, Characterization, and Cytotoxicity of Trifunctional Dinuclear Platinum Complexes: Comparison of Effects of Geometry and Polyfunctionality on Biological Activity," *J. Med. Chem.* 43(16):3189-3192, Jul. 20, 2000.

Serimaa, R., et al., "X-Ray Scattering Study on Amorphous, Polynuclear Platinum Uridine Complexes," *J. Am. Chem. Soc* 115(22):10036-10041, Nov. 3, 1993.

* cited by examiner

*Fig.1.*

PLATINUM CARBOXYLATE ANTICANCER COMPOUNDS

CROSS-REFERENCES TO RELATED APPLICATIONS

This application claims the benefit of U.S. Provisional Application 60/659,932, filed Mar. 10, 2005, and U.S. Provisional Application No. 60/553,108, filed Mar. 15, 2004.

FIELD OF THE INVENTION

The present invention relates to platinum carboxylate compounds, compositions that include the compounds, and methods of treating cancer using the compounds.

BACKGROUND OF THE INVENTION

Cisplatin, cis-[$PtCl_2(NH_3)_2$], is one of the most widely used anti-tumor drugs. Cisplatin is a square-planar Pt (II) complex featuring two inert Pt—N bonds and two relatively labile Pt—Cl bonds. The electrophilic character of the central platinum atom allows cis-[$PtCl_2(NH_3)_2$] to enter a cell to react with nucleophilic groups of the cellular components. A number of observations indicate that the anti-tumor activity of cisplatin is related to its ability to bind to DNA through sequential replacements of the chloride ligands by the $N_7$ atoms of the guanine or the adenine bases.

The Physicians' Desk Reference reports that cisplatin (commercial name, Platinol) can be used to treat testicular, ovarian, and bladder cancers. Methods of treating cancer using cisplatin and cisplatin analogs are described in U.S. Pat. No. 4,177,263, among other publications. Cisplatin is administered intravenously and is transported throughout the body by the blood stream. Cisplatin reaches cancer cells mainly as a neutral molecule and is believed to enter the cell mainly through passive diffusion. Inside the cell, hydrolysis replaces one or both chlorines with water molecules (aquation). The intermediate monoaquated species, [$PtCl(H_2O)(NH_3)_2$]$^+$, is the most active/reactive species responsible for the cytotoxic action of cisplatin. The final product of cisplatin hydrolysis is [$Pt(OH)_2(NH_3)_2$], which is inactive.

Cisplatin, although a very potent and successful antineoplastic, is very toxic. Nephrotoxicity and ototoxicity are dose-limiting factors, and other toxic manifestations include severe nausea and vomiting. The severe toxicity of cisplatin coupled with the development over time of cisplatin-resistant tumors has led to the search for, and development of, improved platinum-based drugs. Desired properties of new and improved platinum drugs include a broader spectrum of activity, particularly against cisplatin-resistant tumors (e.g., lung, breast and colon cancers); an improved therapeutic index, either through greater efficacy or reduced toxicity; and/or modified pharmacological properties to improve drug delivery.

Several second generation platinum anti-cancer compounds, for example, carboplatin(cis-diamine[1,1-cyclobutanedicarboxylato(2-)]—O,O'-platinum (II)), oxaliplatin, iproplatin, and tetraplatin, have been developed. Carboplatin was the second platinum anticancer drug to be approved for clinical use and is less toxic than cisplatin. However, carboplatin is also less active against tumors, requiring higher dosing, and is affected by the same resistance mechanism. Iproplatin and tetraplatin are as active as carboplatin, but are more toxic. Oxaliplatin is more toxic than carboplatin, but has shown promising activity in gastrointestinal tumors, in patients with ovarian cancer who have previously received cisplatin, and in advanced, cisplatin-resistant non-small cell lung patients.

Limitations in second generation platinum drugs have led to the development of third generation compounds, including chelates containing 1,2-diaminocyclohexane (DACH), and promising non-classic (trans- and multinuclear) platinum complexes.

Multinuclear platinum compounds represent innovative structures designed and investigated with the aim of discovering new platinum compounds that are structurally dissimilar to cisplatin and possibly characterized by innovative mechanisms of DNA interaction. Various polynuclear platinum complexes with anti-cancer activity have been described and are currently in clinical trials. One example of a multinuclear platinum compound is BBR3464 (see U.S. Pat. No.6,011,166; Manzotti et al., Cancer Res. 6:2626, 2000). In preclinical studies, BBR3464 exhibited a very high biological activity against cisplatin-resistant tumor cell lines, but toxic side effects were dose limiting. Fewer than 1% of the platinum complexes tested for pre-clinical anti-cancer activity have entered clinical trials in the past 20 years (Perez et al., Curr. Med. Chem.-Anti-Cancer Agents 2 (4): 539:551, 2002).

Accordingly, despite the advances that have been made in the development of alternative platinum compounds, there exists a need in the art for platinum compounds that are as active as cisplatin, have lower toxicity than cisplatin, and that are effective against cisplatin resistant tumors.

SUMMARY OF THE INVENTION

The present invention provides platinum compounds, compositions that include the platinum compounds, methods for making the platinum compounds, and methods for treating cancer by administering the platinum compounds.

In one aspect of the invention, platinum compounds are provided. The platinum compounds are platinum carboxylate compounds in which platinum is covalently coordinated through one or more carboxylate groups. In one embodiment, the platinum compounds of the invention are dinuclear platinum compounds. In one embodiment, the platinum compounds of the invention are mononuclear platinum compounds.

In one embodiment, the invention provides diplatinum C4–C7 cycloalkane diaminetetraacetic acid compounds having formula (I).

In formula (I), $X_1$ and $X_2$ are independently selected from ammonia, amino, nitro, C1–C6 alkoxy, hydroxy, chloride, bromide, or iodide; $Y_1$ and $Y_2$ are independently a direct bond from the cycloalkane ring to the nitrogen atom or independently selected from C1–C6 straight chain or branched alkyl groups; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, 3, 4, or 5, n=0, 1, 2, 3, 4, or 5, provided that m+n≧2 and m+n≦5.

In another embodiment, the invention provides monoplatinum C4–C7 cycloalkane diaminetetraacetic acid compounds having formula (II).

(II)

In formula (II), M is hydrogen or a metal ion, such as sodium or potassium; $Y_1$ and $Y_2$ are the same and are either a direct bond from the cycloalkane ring to the nitrogen atom or a methylene (i.e., —CH$_2$—) group; and n=0, 1, 2, or 3.

In another embodiment, the invention provides diplatinum C4–C7 cycloalkane tetracarboxylate compounds having formula (III).

(III)

In formula (III), $X_1$, $X_2$, $X_3$, and $X_4$ are independently selected from ammonia, amino, nitro, C1–C6 alkoxy, hydroxy, chloride, bromide, or iodide; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, or 3, n=0, 1, 2, or 3, provided that m+n≧0 and m+n≦3.

In another embodiment, the invention provides monoplatinum C4–C7 cycloalkane tetracarboxylate compounds having formula (IV).

(IV)

In formula (IV), M is hydrogen or a metal ion, such as sodium or potassium; $X_1$ and $X_2$ are independently selected from ammonia, amino, nitro, C1–C6 alkoxy, hydroxy, chloride, bromide, or iodide; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, or 3, n=0, 1, 2, or 3, provided that m+n≧0 and m+n≦3.

In another aspect, the invention provides methods for making the platinum compounds.

In a further aspect, the invention provides compositions that include a platinum compound of the invention (e.g., a compound of formulas (I)–(IV)). The compositions include one or more of the platinum compounds, a pharmaceutically acceptable carrier or diluent, and optionally, one or more additional therapeutic agents. The compositions are useful for the administration of platinum compounds to treat cancer.

In another aspect of the invention, methods for treating cancer by administration of a platinum compound of the invention (e.g., a compound of formulas (I)–(IV)) are provided. In the method, a therapeutically effective amount of a platinum compound of the invention is administered to a subject in need thereof.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention provides platinum compounds, compositions that include the platinum compounds, methods for making the platinum compounds, and methods for treating cancer by administering the platinum compounds.

In one aspect of the invention, platinum compounds are provided. The present invention provides mononuclear and dinuclear platinum (II) compounds. As used herein, the term "mononuclear platinum compound" refers to a compound that includes one platinum atom, and the term "dinuclear platinum compound" refers to a compound that includes two platinum atoms. The platinum compounds of the invention are platinum carboxylate compounds in which a platinum atom is covalently coordinated through one or more carboxylate groups.

The invention provides mono- and diplatinum C4–C7 cycloalkane diaminetetraacetic acid compounds. As used herein, the term "monoplatinum C4–C7 cycloalkane diaminetetraacetic acid compound" refers to a compound that includes one platinum atom and a C4–C7 cycloalkane (i.e., cyclobutane, cyclopentane, cyclohexane, and cycloheptane) moiety having two aminodiacetic acid (i.e., —N(CH$_2$CO$_2$)$_2$) groups in which the platinum atom is coordinated by one or more of the aminoacetic acid groups. The term "diplatinum C4–C7 cycloalkane diaminetetraacetic acid compound" refers to a compound that includes two platinum atoms and a C4–C7 cycloalkane (i.e., cyclobutane, cyclopentane, cyclohexane, and cycloheptane) moiety having two aminodiacetic acid (i.e., —N(CH$_2$CO$_2$)$_2$) groups in which the platinum atom is coordinated by one or more of the aminoacetic acid groups.

In one embodiment, the invention provides diplatinum C4–C7 cycloalkane diaminetetraacetic acid compounds having formula (I).

In formula (I), $X_1$ and $X_2$ are independently selected from ammonia ($NH_3$), amino ($NR_2$), nitro ($NO_3$), C1–C6 alkoxy (OR), hydroxy (OH), chloride (Cl), bromide (Br), or iodide (I), where R is a C1–C6 straight chain or branched alkyl group; $Y_1$ and $Y_2$ are independently a direct bond from the cycloalkane ring to the nitrogen atom or independently selected from C1–C6 straight chain or branched alkyl groups; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, 3, 4, or 5, n=0, 1, 2, 3, 4, or 5, provided that m+n≧2 and m+n≦5.

In one embodiment of formula (I), $X_1$ and $X_2$ are independently selected from ammonia and hydroxy.

Figure 1:
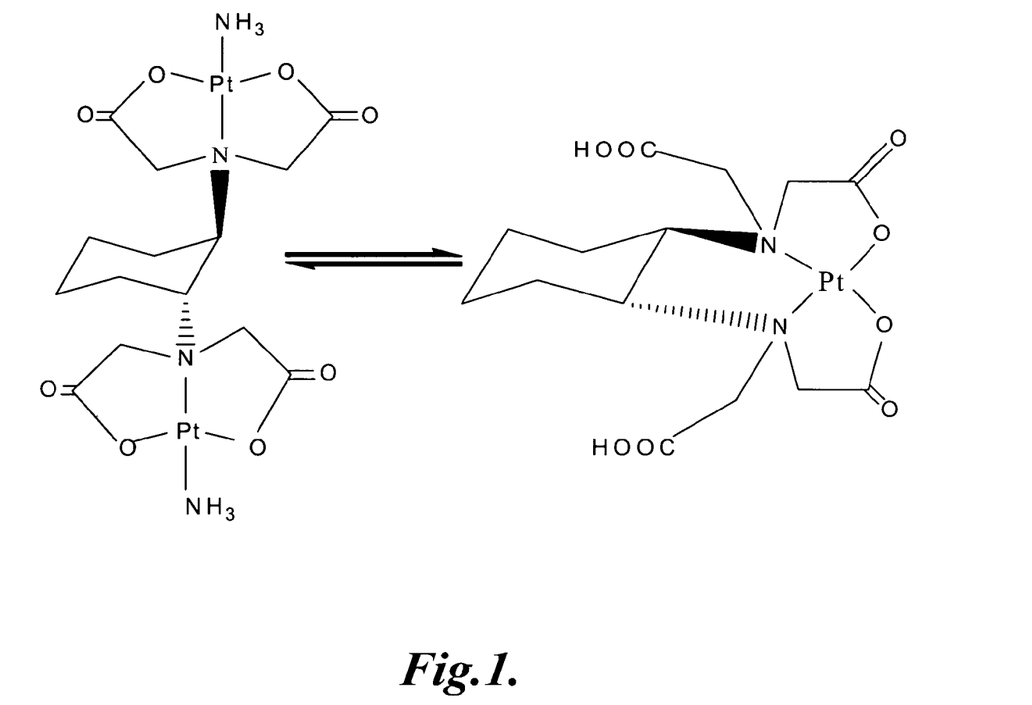
FIG. 1 is a schematic illustration of two representative platinum compounds of the invention, a dinuclear platinum compound and a mononuclear platinum compound.

In one embodiment of formula (I), $X_1$ and $X_2$ are ammonia, $Y_1$ and $Y_2$ are direct bonds; m=0, n=4, and $Z_2$ is —$CH_2$— (see FIG. 1).

In another embodiment, the invention provides monoplatinum C4–C7 cycloalkane diaminetetraacetic acid compounds having formula (II).

In formula (II), M is hydrogen or a metal ion, such as sodium or potassium; $Y_1$ and $Y_2$ are the same and are either a direct bond from the cycloalkane ring to the nitrogen atom or a methylene (i.e., —$CH_2$—) group; and n=0, 1, 2, or 3.

In one embodiment of formula (II), M is hydrogen or a metal ion, $Y_1$ and $Y_2$ are direct bonds, and n=2 (see FIG. 1).

Representative platinum diaminetetraacetic acid compounds of the invention include compounds having formulas (I) and (II). It will be appreciated that the compounds of formula (I) have a variety of substitution patterns (i.e., positional isomers for the amine substituents). Representative substitution patterns include, for example, 1,2-diaminetetraacetic acid substitution for cyclobutane, cyclopentane, cyclohexane, and cycloheptane compounds (i.e., m=0 and n=2, 3, 4, and 5, respectively, or n=0 and m=2, 3, 4, and 5, respectively); 1,3-diaminetetraacetic acid substitution for cyclobutane, cyclopentane, cyclohexane, and cycloheptane compounds (i.e., m=1 and n=1, 2, 3, 4, respectively, or n=1 and m=1, 2, 3, 4, respectively); and 1,4-diaminetetraacetic acid substitution for cyclohexane and cycloheptane compounds (i.e., m=2 and n=2 and 3, respectively, or n=2 and m=2 and 3, respectively). It will be appreciated that geometric isomers are also within the scope of the invention. Geometric isomers include cis and trans isomers. For 1,2-substitution, the compound is a trans isomer. For 1,3- and 1,4-substitution, the compound may be either a cis or trans isomers. A representative compound of the invention is cyclohexane-trans-1,2-diaminetetraacetic-acid-diplatinum (formula (I): $Y_1$ and $Y_2$ are direct bonds having a trans relationship; m=0; n=4; and Z is —$CH_2$—; see FIG. 1).

The cycloalkane portion of the platinum compounds of the invention (e.g., formulas (I) and (II)) may optionally be substituted. Suitable substituents do not interfere with platinum coordination and are not chemically reactive with platinum (e.g., reduced by platinum). Representative substituents include C1–C6 straight chain or branched alkyl groups.

In one embodiment, the present invention provides a cyclohexane-trans-1,2-diaminetetraacetic-acid-diplatinum compound (formula (I): $Y_1$ and $Y_2$ are direct bonds having a trans relationship; m=0; n=4; and Z is —$CH_2$—), which is the product resulting from the reaction of two equivalents of cis-diaminedinitroplatinum (II) with one equivalent of the tetrasodium salt of cyclohexane-trans-1,2-diaminetetraacetic acid. The preparation of cyclohexane-trans-1,2-diaminetetraacetic-acid-diplatinum is described in Example 1.

FIG. 1 illustrates the structure of a cyclohexane-trans-1,2-diaminetetraacetic-acid-diplatinum compound. The infrared (IR) spectrum for cyclohexane-trans-1,2-diaminetetraacetic-acid-diplatinum exhibits N—H (3279 $cm^{-1}$), coordinated carboxyl groups (1638 $cm^{-1}$ and 1400 $cm^{-1}$), and no —COOH stretching (1700–1750 $cm^{-1}$). The carboxyl group frequencies are compatible with chelated structures of known oxalate complexes. The molecular weight of cyclohexane-trans-1,2-diaminetetraacetic-acid-diplatinum was determined using electrospray ionization-mass spectrometry (ESI-MS). The mass spectrum with the characteristic isotopic abundance pattern for platinum indicates the presence of two platinum atoms in the compound.

In another embodiment, the present invention provides a cyclohexane-trans-1,2-diaminetetraacetic-acid-monoplatinum compound (formula (II): M is hydrogen, $Y_1$ and $Y_2$ are direct bonds, and n=2, see FIG. 1), which is the product resulting from the reaction of one equivalent of cis-diaminedinitroplatinum (II) with one equivalent of the tetrasodium salt of cyclohexane-trans-1,2-diaminetetraacetic acid. The preparation of cyclohexane-trans-1,2-diaminetetraacetic-acid-monoplatinum is described in Example 2.

In another embodiment, the invention provides mono- and diplatinum C4–C7 cycloalkane tetracarboxylate compounds. As used herein, the term "monoplatinum C4–C7 cycloalkane tetracarboxylate compound" refers to a compound that includes one platinum atom and a C4–C7 cycloalkane (i.e., cyclobutane, cyclopentane, cyclohexane, and cycloheptane) moiety having four carboxylate groups in which the platinum atom is coordinated by one or more of the carboxylate groups. The term "diplatinum C4–C7 cycloalkane tetracarboxylate compound" refers to a compound that includes two platinum atoms and a C4–C7 cycloalkane (i.e., cyclobutane, cyclopentane, cyclohexane, and cycloheptane) moiety having four carboxylate groups in which the platinum atoms are coordinated by one or more of the carboxylate groups.

In one embodiment, the invention provides diplatinum C4–C7 cycloalkane tetracarboxylate compounds having formula (III).

(III)

In formula (III), $X_1$, $X_2$, $X_3$, and $X_4$ are independently selected from ammonia ($NH_3$), amino ($NR_2$), nitro ($NO_3$), C1–C6 alkoxy (OR), hydroxy (OH), chloride (Cl), bromide (Br), or iodide (I), where R is a C1–C6 straight chain or branched alkyl group; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, or 3, n=0, 1, 2, or 3, provided that $m+n \geq 0$ and $m+n \leq 3$.

In one embodiment of formula (III), $X_1$, $X_2$, $X_3$, and $X_4$ are independently selected from ammonia and hydroxy, and m=0 and n=0.

In another embodiment of formula (III), $X_1$, $X_2$, $X_3$, and $X_4$ are independently selected from ammonia and hydroxy, and m=1 and n=0.

In another embodiment of formula (III), $X_1$, $X_2$, $X_3$, and $X_4$ are independently selected from ammonia and hydroxy, and m=0 and n=2.

In another embodiment, the invention provides monoplatinum C4–C7 cycloalkane tetracarboxylate compounds having formula (IV).

(IV)

In formula (IV), M is hydrogen or a metal ion, such as sodium or potassium; $X_1$ and $X_2$ are independently selected from ammonia, amino, nitro, C1–C6 alkoxy, hydroxy, chloride, bromide, or iodide; $Z_1$ is $C(R_1)R_2$, wherein $R_1$ and $R_2$ are independently hydrogen or C1–C6 straight chain or branched alkyl; $Z_2$ is $C(R_3)R_4$, wherein $R_3$ and $R_4$ are independently hydrogen or C1–C6 straight chain or branched alkyl; and m=0, 1, 2, or 3, n=0, 1, 2, or 3, provided that $m+n \geq 0$ and $m+n \leq 3$.

Representative platinum cycloalkane tetracarboxylate compounds of the invention include compounds having formulas (III) and (IV). It will be appreciated that the compounds of formula (III) and (IV) have a variety of substitution patterns (i.e., positional isomers for the carboxylate substituents). Representative substitution patterns include, for example, 1,2,3,4-tetracarboxylate substitution for cyclobutane, cyclopentane, cyclohexane, and cycloheptane compounds (i.e., m=0 and n=0, 1, 2, and 3, respectively, or n=0 and m=0, 1, 2, and 3, respectively); and 1,2,4,5-tetracarboxylate substitution for cyclohexane and cycloheptane compounds (i.e., m=1 and n=1 and 2, respectively, or n=1 and m=1 and 2, respectively). Representative substitution patterns include geminal (e.g., 1,1-) substitution patterns, for example, 1,1,2,2-, 1,1,3,3-, and 1,1,4,4-tetracarboxylate substitutions. Combinations of vicinal (e.g., 1,2-) substitution and geminal (e.g., 3,3-) substitution patterns are within the scope of the invention. It will be appreciated that geometric isomers are also within the scope of the invention. Geometric isomers include cis and trans isomers.

The cycloalkane portion of the platinum compounds of the invention (e.g., formulas (III) and (IV)) may optionally be substituted. Suitable substituents do not interfere with platinum coordination and are not chemically reactive with platinum (e.g., reduced by platinum). Suitable substituents include C1–C6 straight chain or branched alkyl groups.

In one embodiment, the present invention provides a cyclopentane-1,2,3,4-tetracarboxylic-acid-diplatinum compound, which is the product resulting from the reaction of two equivalents of cis-diaminedinitroplatinum (II) with one equivalent of the tetrasodium salt of cyclopentane-1,2,3,4-tetracarboxylic acid. The preparation of cyclopentane-1,2,3,4-tetracarboxylic-acid-diplatinum is described in Example 3.

In another embodiment, the present invention provides a cyclopentane-1,2,3,4-tetracarboxylic acid-monoplatinum compound, which is the product resulting from the reaction of one equivalent of cis-diaminedinitroplatinum (II) with one equivalent of the tetrasodium salt of cyclopentane-1,2,3,4-tetracarboxylic acid. The preparation of cyclopentane-1,2,3,4-tetracarboxylic acid-monoplatinum is described in Example 4.

In another embodiment, the present invention provides a cyclobutane-1,2,3,4-tetracarboxylic acid-diplatinum compound, which is the product resulting from the reaction of two equivalents of the cis-diaminedinitroplatinum (II) with one equivalent of the tetrasodium salt of cyclobutane-1,2,3,4-tetracarboxylic acid. The preparation of cyclobutane-1,2,3,4-tetracarboxylic-acid-diplatinum is described in Example 5.

In another embodiment, the present invention provides cyclobutane-1,2,3,4-tetracarboxylic acid-monoplatinum compound, which is the product resulting from the reaction of one equivalent of cis-diaminedinitroplatinum (II) with one equivalent of the tetrasodium salt of cyclobutane-1,2,3,4-tetracarboxylic acid. The preparation of cyclobutane-1,2,3,4-tetracarboxylic acid-monoplatinum is described in Example 6.

In another aspect of the invention, methods for making the mononuclear and dinuclear platinum compounds are provided. The platinum compounds of the invention are prepared by reaction of a suitably reactive platinum compound with a polycarboxylic acid (or salt). Suitably reactive platinum compounds are those platinum compounds that are reactive toward carboxylic acids (or their salts). Suitable platinum compounds include, for example, cis-diaminedichloroplatinum (II) (cisplatin), and compounds derived from cisplatin, for example, cis-diaminedinitroplatinum (II) and cis-diaminemonochloromononitroplatinum (II). Suitable polycarboxylic acids include, for example, cyclohexane-trans-diaminetetraacetic acid; cyclopentane-1,2,3,4-tetracarboxylic acid; and cyclobutane-1,2,3,4-tetracarboxylic acid.

In one aspect, the present invention provides a dinuclear platinum compound formed by combining a suitably reactive platinum compound (e.g., cis-diaminedinitroplatinum (II)) with a diaminetetraacetic acid compound.

In one embodiment, the dinuclear platinum compound is obtained by treating the tetrasodium salt of cyclohexane-trans-1,2-diaminetetraacetic acid with cis-diaminedinitroplatinum (II). In the method, one equivalent of the tetrasodium salt of cyclohexane-trans-1,2-diaminetetraacetic acid is treated with two equivalents of cis-diaminedinitroplatinum (II) to provide the dinuclear compound. In one embodiment, a solution of the tetrasodium salt of cyclohexane-trans-1,2-diaminetetraacetic acid (pH about 6.5) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product dinuclear platinum compound can be isolated from the reaction mixture by precipitation upon the addition of methanol to provide a white solid that can be collected by filtration, washed with water and then acetone, and dried under vacuum. A representative procedure for making the dinuclear platinum compound is described in Example 1.

In another aspect, the present invention provides a mononuclear platinum compound formed by combining a suitably reactive platinum compound (e.g., cis-diaminedinitroplatinum (II)) with a diaminetetraacetic acid compound.

In one embodiment, the mononuclear platinum compound is obtained by treating the tetrasodium salt of cyclohexane-trans-1,2-diaminetetraacetic acid with cis-diaminedinitroplatinum (II). In the method, one equivalent of the tetrasodium salt of cyclohexane-trans-1,2-diaminetetraacetic acid is treated with one equivalent of cis-diaminedinitroplatinum (II) to provide the mononuclear compound. In one embodiment, a solution of the tetrasodium salt of cyclohexane-trans-1,2-diaminetetraacetic acid (pH about 6.5) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product mononuclear platinum compound can be isolated from the reaction mixture by precipitation upon the addition of methanol to provide a white solid that can be collected by filtration, washed with water and then acetone, and dried under vacuum. A representative procedure for making the mononuclear platinum compound is described in Example 2.

In another aspect, the present invention provides dinuclear platinum compounds formed by combining a suitably reactive platinum compound (e.g., cis-diaminedinitroplatinum (II)) with a cycloalkane tetracarboxylic acid (e.g., cyclopentane-1,2,3,4-tetracarboxylic acid, cyclobutane-1,2,3,4-tetracarboxylic acid).

In one embodiment, a dinuclear platinum compound is obtained by treating the tetrasodium salt of cyclopentane-1,2,3,4-tetracarboxylic acid with cis-diaminedinitroplatinum (II). In the method, one equivalent of the tetrasodium salt of cyclopentane-1,2,3,4-tetracarboxylic acid is treated with two equivalents of cis-diaminedinitroplatinum (II) to provide the dinuclear compound. In one embodiment, a solution of the tetrasodium salt of cyclopentane-1,2,3,4-tetracarboxylic acid (pH about 6.5) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product dinuclear platinum compound can be isolated from the reaction mixture by precipitation upon the addition of methanol to provide a pale green solid that can be collected by filtration, washed with water and then acetone, and dried under vacuum. A representative procedure for making the dinuclear platinum compound is described in Example 3.

In another embodiment, a dinuclear platinum compound is obtained by treating the tetrasodium salt of cyclobutane-1,2,3,4-tetracarboxylic acid with cis-diaminedinitroplatinum (II). In the method, one equivalent of the tetrasodium salt of cyclobutane-1,2,3,4-tetracarboxylic acid is treated with two equivalents of cis-diaminedinitroplatinum (II) to provide the dinuclear compound. In one embodiment, a solution of the tetrasodium salt of cyclobutane-1,2,3,4-tetracarboxylic acid (pH about 6.8) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product dinuclear platinum compound can be isolated from the reaction mixture by precipitation upon the addition of methanol to provide a pale white solid that can be collected by filtration, washed with water and then acetone, and dried under vacuum. A representative procedure for making the dinuclear platinum compound is described in Example 5.

In another aspect, the present invention provides mononuclear platinum compounds formed by combining a suitably reactive platinum compound (e.g., cis-diaminedinitroplatinum (II)) with a cycloalkane tetracarboxylic acid.

In one embodiment, a mononuclear platinum compound is obtained by treating the tetrasodium salt of cyclopentane-1,2,3,4-tetracarboxylic acid with cis-diaminedinitroplatinum (II). In the method, one equivalent of the tetrasodium salt of cyclopentane-1,2,3,4-tetracarboxylic acid is treated with one equivalent of cis-diaminedinitroplatinum (II) to provide the mononuclear compound. In one embodiment, a solution of the tetrasodium salt of cyclopentane 1,2,3,4-tetracarboxylic acid (pH about 6.5) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product mononuclear platinum compound can be isolated from the reaction mixture by precipitation upon the addition of methanol to provide a pale green solid that can be collected by filtration, washed with water and then acetone, and dried under vacuum. A representative procedure for making the mononuclear platinum compound is described in Example 4.

In another embodiment, a mononuclear platinum compound is obtained by treating the tetrasodium salt of cyclobutane-1,2,3,4-tetracarboxylic acid with cis-diaminedinitroplatinum (II). In the method, one equivalent of the tetrasodium salt of cyclobutane-1,2,3,4-tetracarboxylic acid is treated with one equivalent of cis-diaminedinitroplatinum (II) to provide the mononuclear compound. In one embodiment, a solution of the tetrasodium salt of cyclobutane-1,2,3,4-tetracarboxylic acid (pH about 6.8) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (e.g., 60° C.) to complete the reaction. The product mononuclear platinum compound can be isolated from the reaction mixture by precipitation upon the addition of methanol to provide a pale white solid that can be collected by filtration, washed with water and then acetone, and dried under vacuum. A representative procedure for making the mononuclear platinum compound is described in Example 6.

In another aspect, the present invention provides methods of treating human or animal subjects suffering from a cellular proliferative disease, such as cancer. Representative cellular proliferative diseases treatable by the compounds of the invention include hematologic cancers, such as leukemia, lymphoma, and myeloma, and nonhematologic cancers, such as solid tumor carcinomas (e.g., breast, ovarian, pancreatic, colon, colorectal, non-small lung and bladder), sarcomas, and gliomas. The present invention provides methods of treating a human or animal subject in need of such treatment, comprising administering to the subject a therapeutically effective amount of one or more platinum compounds of the invention, either alone or in combination with one or more other therapeutic and/or anticancer agents.

The platinum compounds of the invention have cytotoxic activity against cancer cells. In some embodiments, representative platinum compounds of the invention have improved cytotoxic activities against cancer cells as compared to cisplatin or carboplatin as shown in Tables 1 and 2.

In other aspects, the present invention provides methods for treating a cellular proliferative disease in a human or animal subject in need of such treatment, comprising administering to said subject an amount of a platinum compound of the invention effective to reduce or prevent cellular proliferation or tumor growth in the subject.

In yet other aspects, the present invention provides methods for treating a cellular proliferative disease in a human or animal subject in need of such treatment comprising administering to said subject an amount of a platinum compound of the invention effective to reduce or prevent cellular proliferation in the subject in combination with at least one additional agent for the treatment of cancer.

The platinum compounds of the invention, either alone or in combination with other anticancer agents, can be used for the prevention and treatment of cancers such as primary or metastatic melanoma, thymoma, lymphoma, sarcoma, lung cancer (NSCLC and SCLC), gastric cancer, liver cancer, non-Hodgkin's lymphoma, Hodgkin's lymphoma, leukemias, testicular cancer, uterine cancer, cervical cancer, bladder cancer, kidney cancer, colon cancer, colorectal cancer, and adenocarcinomas such as breast cancer, prostate cancer, ovarian cancer, pancreatic cancer.

Compositions that include one or more platinum compounds of the invention are administered to deliver therapeutically effective amounts of the platinum compound. Therapeutically effective amounts of the platinum compound(s) will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the platinum compounds of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the platinum compounds of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Platinum compounds that exhibit large therapeutic indices are particularly suitable in the practice of the methods of the invention. The data obtained from cell culture assays and animal studies may be used in formulating a range of dosage for use in humans or other mammals. The dosage of such platinum compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The platinum compounds of the invention may be administered alone, or in combination with one or more additional therapeutically active agents. For example, in the treatment of cancer, the platinum compounds may be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live Mycobacterium bovis, dicarbazine, asparaginase, leucovorin, mitotane, vincristine, vinblastine, and taxanes (e.g., paclitaxel, docetaxel). Appropriate amounts in each case will vary with the particular agent, and will be either readily known to those skilled in the art or readily determinable by routine experimentation.

Administration of the platinum compounds of the invention is accomplished by any effective route, for example, parenterally or orally. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The platinum compounds of the invention may be injected directly into a tumor, into the vicinity of a tumor, or into a blood vessel that supplies blood to the tumor.

In other aspects, the present invention provides pharmaceutical compositions comprising at least one platinum compound of the invention together with a pharmaceutically acceptable carrier suitable for administration to a human or animal subject, either alone or together with other therapeutics and/or anticancer agents. The platinum compounds of the invention may be formulated into a composition that additionally comprises suitable pharmaceutically acceptable carriers, including excipients and other compounds that facilitate administration of the platinum compounds to a mammalian subject. Further details on techniques for formulation and administration may be found in the latest edition of Remington's Pharmaceutical Sciences, Maack Publishing Co, Easton Pa.

Compositions for oral administration may be formulated using pharmaceutically acceptable carriers well known in the art, in dosages suitable for oral administration. Such carriers enable the compositions containing platinum compounds of the invention to be formulated as tablets, pills, dragees, capsules, liquids, gels, syrups, slurries, and suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate. Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Platinum compounds for oral administration may be formulated, for example, as push-fit capsules made of gelatin, as well as soft, sealed capsules made of gelatin and a coating such as glycerol or sorbitol. Push-fit capsules may contain platinum compounds mixed with filler or binders such as lactose or starches, lubricants such as talc or magnesium stearate, and, optionally, stabilizers. In soft capsules, the platinum compounds may be dissolved or suspended in suitable liquids, such as fatty oils, liquid paraffin, or liquid polyethylene glycol with or without stabilizers.

Compositions for parenteral administration include aqueous solutions of one or more platinum compounds of the invention. For injection, the platinum compounds may be formulated in aqueous solutions, such as in physiologically compatible buffers such as Hank's solution, Ringer's solution, or dextrose solutions. Aqueous injection suspensions may contain substances, which increase the viscosity of the suspension, such as sodium carboxymethyl cellulose, sorbitol, or dextran.

Compositions containing the platinum compounds of the present invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the platinum compounds may be provided as a salt and can be formed with many acids, including but not limited to hydrochloric, sulfuric, acetic, lactic, tartaric, malic, succinic. Salts tend to be more soluble in aqueous or other protonic solvents than are the corresponding free base forms.

After compositions formulated to contain the platinum compounds and an acceptable carrier have been prepared, they can be placed in an appropriate container and labeled for use.

In another aspect of the invention, a kit is provided that includes one or more compounds of the invention in one or more containers. A representative kit includes a container that includes a quantity of a compound of the invention and a package insert or other labeling including directions for treating a cellular proliferative disease by administering a quantity of the compound.

The following examples are provided for the purpose of illustrating, not limiting, the invention.

EXAMPLES

Example 1

Preparation of Cyclohexane-trans-1,2-diaminetetraacetic-acid-diplatinum

Step 1. Silver nitrate (Aldrich, USA) solution (3.44 g dissolved in 100 ml water) was added to cisplatin (Saiquest, India) ([Pt(NH$_3$)$_2$Cl$_2$]) solid (3.08 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclohexane-trans-1,2-diaminetetraacetic acid (TCI, USA) (1.86 g) was neutralized to pH about 6.5 using 1N NaOH to yield a clear solution. The resulting sodium cyclohexane-trans-1,2-diaminetetraacetate solution was maintained at 60° C. and the cisplatin nitrate solution from Step 1 was added to it. The reaction mixture was kept under stirring at 60° C. for one hour. The solution was filtered to remove any residual silver. The filtrate was kept under stirring at about 60° C. for another one hour. After an hour, heat was turned off and the solution was allowed to stir for another half hour. The reaction mixture was clear and yellow.

Step 3. The reaction mixture from Step 2 was precipitated using methanol to give a white precipitate. The precipitate was centrifuged (6000 rpm) and extracted and a final washing was done with acetone. The product was allowed to air dry in the hood overnight. The following day the white precipitate was put in the vacuum oven overnight to remove any residual moisture.

IR$\nu_{max}^{KBr}$cm$^{-1}$: 3279, 1638, 1335, 908.

MS (Positive ESI): m/z 767 diplatinum (M+H)$^+$; m/z 540 monoplatinum (M+H)$^+$.

Elemental Analysis. Calculated: C, 21; H, 3.27; N, 7.00; Pt, 48.74; Observed: C, 20.40; H, 3.61; N, 7.30; Pt, 48.6

The product of the process described above is a mixture of cyclohexane-trans-1,2-diaminetetraacetic-acid-diplatinum and cyclohexane-trans- 1,2-diaminetetraacetic-acid-monoplatinum in a ratio of about 1:1.

Example 2

Preparation of Cyclohexane-trans-1,2-diaminetet-raacetic-acid-monoplatinum

Step 1. Silver nitrate (Aldrich, USA) solution (1.72 g dissolved in 50 ml water) was added to cisplatin (Saiquest, India) ([Pt(NH$_3$)$_2$Cl$_2$]) solid (1.54 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclohexane-trans-1,2-diaminetetraacetic acid (TCI, USA) (1.86 g) was neutralized to pH about 6.5 using 1N NaOH to yield a clear solution. The resulting sodium cyclohexane-trans-1,2-diaminetetraacetate solution was maintained at 60° C. and the cisplatin nitrate solution from Step 1 was added to it. The reaction mixture was kept under stirring at 60° C. for one hour. The solution was filtered to remove any residual silver. The filtrate was kept under stirring at about 60° C. for another one hour. After an hour, heat was turned off and the solution was allowed to stir for another half hour. The reaction mixture was clear and yellow at this time.

Step 3. The reaction mixture from Step 2 was precipitated using methanol to give a white precipitate. The precipitate was centrifuged (6000 rpm) and extracted and a final washing was done with acetone. The product was allowed to air dry in the hood overnight. The following day the white precipitate was put in the vacuum oven overnight to remove any residual moisture.

Example 3

Preparation of Cyclopentane-1,2,3,4-tetracarboxylic acid-diplatinum

Step 1. Silver nitrate (Aldrich, USA) solution (2.26 g dissolved in 100 ml water) was added to cisplatin (Saiquest, India) ([Pt(NH$_3$)$_2$Cl$_2$]) solid (2 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclopentane-1,2,3,4-tetracarboxylic acid (Aldrich, USA) (0.8 g) was neutralized to pH about 6.5 using 1N NaOH to yield a clear solution. The resulting sodium cyclopentane-tetracarboxylate solution was maintained at 60° C. and the cisplatin nitrate solution from Step 1 was added to it, resulting in the formation of pale greenish white precipitate. The resulting reaction mixture was then cooled to room temperature and then refrigerated overnight to ensure complete precipitation.

Step 3. The following day, the precipitate from Step 2 was centrifuged (6000 rpm) and extracted with water (6×50 ml) and the final washing was done with acetone. The product was allowed to air dry in the hood overnight. The following day the pale green precipitate was put in the vacuum oven overnight to remove any residual moisture.

Example 4

Preparation of Cyclopentane-1,2,3,4-tetracarboxylic acid-monoplatinum

Step 1. Silver nitrate (Aldrich, USA) solution (1.13 g dissolved in 50 ml water) was added to cisplatin (Saiquest, India) ([Pt(NH$_3$)$_2$Cl$_2$]) solid (1 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclopentane-1,2,3,4-tetracarboxylic acid (Aldrich, USA) (0.8 g) was neutralized to pH about 6.5 using 1N NaOH to yield a clear solution. The resulting sodium cyclopentane-tetracarboxylate solution was maintained at 60° C. and the cisplatin nitrate solution from Step 1 was added to it, resulting in the formation of pale greenish white precipitate. The resulting reaction mixture was then cooled to room temperature and then refrigerated overnight to ensure complete precipitation.

Step 3. The following day, the precipitate from Step 2 was centrifuged (6000 rpm) and extracted with water (6×50 ml) and the final washing was done with acetone. The product was allowed to air dry in the hood overnight. The following day the pale green precipitate was put in the vacuum oven overnight to remove any residual moisture.

Example 5

Preparation of Cyclobutane-1,2,3,4-tetracarboxylic acid-diplatinum

Step 1. Silver nitrate (Aldrich, USA) solution (1.13 g dissolved in 50 ml water) was added to cisplatin (Saiquest, India) ([Pt(NH$_3$)$_2$Cl$_2$]) solid (1 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclobutane-1,2,3,4-tetracarboxylic acid (Aldrich, USA) (0.386 g) was neutralized to pH about 6.8 using 1N NaOH to yield a clear solution. The resulting sodium cyclobutane-tetracarboxylate solution was maintained at 60° C. and the cisplatin nitrate solution from Step 1 was added to it, resulting in the formation of pale white precipitate. The resulting reaction mixture was then cooled to room temperature and then refrigerated overnight to ensure complete precipitation.

Step 3. The following day, the precipitate from Step 2 was centrifuged (6000 rpm) and extracted with water (6×50 ml) and the final washing was done with acetone. The product was allowed to air dry in the hood overnight. The following day the grayish pale white precipitate was put in the vacuum oven overnight to remove any residual moisture.

Example 6

Preparation of Cyclobutane-1,2,3,4-tetracarboxylic acid-monoplatinum

Step 1. Silver nitrate (Aldrich, USA) solution (0.565 g dissolved in 50 ml water) was added to cisplatin (Saiquest, India) ([Pt(NH$_3$)$_2$Cl$_2$]) solid (0.5 g) in a conical flask with constant stirring. The entire solution was kept under stirring at about 60° C. until the silver chloride precipitation was complete and the mother liquor was almost colorless (about one hour). The precipitate was then filtered off using a 0.45 micron disposable filter. The filtrate was again heated to 60° C. for 30 minutes to ensure complete precipitation of silver chloride. The solution was again filtered using a 0.45 micron disposable filter.

Step 2. Cyclobutane-1,2,3,4-tetracarboxylic acid (Aldrich, USA) (0.386 g) was neutralized to pH about 6.8 using 1N NaOH to yield a clear solution. The resulting sodium cyclobutane-tetracarboxylate solution was maintained at 60° C. and the cisplatin nitrate solution from Step 1 was added to it, resulting in the formation of pale white precipitate. The resulting reaction mixture was then cooled to room temperature and then refrigerated overnight to ensure complete precipitation.

Step 3. The following day, the precipitate from Step 2 was centrifuged (6000 rpm) and extracted with water (6×50 ml) and the final washing was done with acetone. The product was allowed to air dry in the hood overnight. The following day the grayish pale white precipitate was put in the vacuum oven overnight to remove any residual moisture.

Example 7

Cytotoxic Screening of Representative Platinum Compounds

ALAMAR BLUE Assay. Cytotoxicity was tested for each of four compounds: cisplatin, carboplatin, cyclohexane-trans-1,2-diaminetetraacetic-acid-diplatinum (CDTA-diplatinum), prepared as described in Example 1, and cyclohexane-trans-1,2-diaminetetraacetic-acid-monoplatinum (CDTA-monoplatinum), prepared as described in Example 2. Cytotoxicity was tested by measuring the amount of compound required to inhibit cell growth by 50% (GI$_{50}$ value). Cytotoxicity was measured in two cell lines: a colorectal carcinoma cell line (HCT-116); and a non-small cell lung cancer cell line (NCI-H460). The marker used to quantify cell growth inhibition was ALAMAR BLUE, a non-fluorescent blue dye that is reduced to a fluorescent red product by viable cells. The amount of fluorescence is proportional to the number of viable cells.

Screening in HCT-116 cells. HCT-116 colorectal carcinoma cells (ATCC # CCL-247) were inoculated into a set of twenty-four 96-well microtiter plates containing 100 μl of McCoy's 5A media (HyClone, Logan, Utah) per well to a plating density of 7500 cells per well. After cell inoculation, the microtiter plates were incubated at 37° C., 5% CO$_2$, 95% air and 100% relative humidity for 24 hours. After 24 hours incubation, ALAMAR BLUE reagent (Biosource, Camarillo, Calif.) was added to two plates to a final concentration of 10% v/v in each well. The plates were returned to the incubator for 4 hours and then read in a Perkin Elmer HTS 7000 Bio Assay Reader using an excitation wavelength of 535 nm and an emission wavelength of 590 nm to determine the cell population at the time of drug addition—time zero.

Cisplatin, CDTA-diplatinum, and CDTA-monoplatinum were each solubilized in 0.9% saline and diluted in McCoy's 5A media to a concentration of 8×10$^{-6}$ M. A series of 10-fold dilutions were made in media to provide a total of five drug concentrations for each drug: 8×10$^{-6}$ M; 8×10$^{-7}$ M; 8×10$^{-8}$ M; 8×10$^{-9}$ M; and 8×10$^{-10}$ M. Carboplatin was solubilized in 0.9% saline and diluted in media to a concentration of 1.5×10$^{-3}$ M. A series of 10-fold dilutions were made in media to provide a total of five drug concentrations: 1.5×10$^{-3}$ M; 1.5×10$^{-4}$ M; 1.5×10$^{-5}$ M; 1.5×10$^{-6}$ M; and 1.5×10$^{-7}$ M. Aliquots of 100 μl of each drug concentration, one concentration per plate, were added to the wells of the microtiter plates prepared above containing the HCT-116 cells. Two no-drug control plates were also prepared.

Following drug addition, the plates were incubated for an additional 48 hours at the conditions above.

After 48 hours of incubation the plates were removed and ALAMAR BLUE reagent was added to a final concentration of 10% v/v to each well. The plates were returned to the incubator for 4 hours and read in the Bio Assay Reader as described above.

Screening in NCI-H460 cells. The screening protocol above was repeated using NCI-H460 non-small cell lung cancer cells (ATCC # HTB-177) plated to a density of 10,000 cells per well in RPMI media (Mediatech, Inc., Herndon, Va.).

Results. The GI$_{50}$ value, the concentration of drug required to inhibit 50% of cell growth, was calculated for each cell line and is summarized in Table 1 below.

TABLE 1

Summary of GI$_{50}$ Values.

| Platinum Compound | HCT-116 | H-460 |
|---|---|---|
| Cisplatin | 4 μM | 469 μM |
| Carboplatin | 159 μM | 9 μM |
| CDTA-diplatinum | 550 nM | 371 nM |
| CDTA-monoplatinum | 6.4 μM | 9.71 μM |

As shown in Table 1, the representative diplatinum compound of the invention exhibited a significantly lower GI$_{150}$ value compared to either cisplatin or carboplatin for both colorectal carcinoma and non-small cell lung cancer cell lines. The representative monoplatinum compound of the invention exhibited a GI$_{50}$ value comparable to cisplatin and a significantly lower value than for carboplatin for the colorectal carcinoma cell line, and a GI$_{50}$ value comparable to carboplatin and a significantly lower value than for cisplatin for the non-small cell lung cancer cell line.

MTS Assay. Cytotoxicity was tested for cisplatin; cyclohexane-trans-1,2-diaminetetraacetic-acid-diplatinum (CDTA-diplatinum), prepared as described in Example 1; and cyclohexane-trans-1,2-diaminetetraacetic-acid-monoplatinum (CDTA-monoplatinum), prepared as described in Example 2. Cytotoxicity was tested by measuring the amount of compound required to inhibit cell growth by 50% (GI$_{50}$ value). Cytotoxicity was measured in six cell lines: two colorectal carcinoma cell lines, HT29 (ATCC # CCL-218) and HCT-116 (ATCC # CCL-247); two small cell lung cancer cell lines, NCI-H69 (ATCC # HTB-119) and NCI-H69/AR (ATCC # CRL-11351); and two ovarian cancer cell lines, A2780 (ECACC # 93112519) and A2780/DPPt (similar strain, A2780 cis, available at ECACC # 93112517). Viable cell number was measured using the MTS cell viability assay (CELLTITER 96 AQ$_{ueous}$ One Solution Cell Proliferation Assay kit available from Promega, USA). Cell growth inhibition was quantified by measuring absorbance at 490 nm, which is directly proportional to the number of living cells in culture.

The platinum compounds were prepared as 10 mM stock solutions in water containing 5% dextrose (D5W). Cisplatin was prepared in saline. Dosing solutions were prepared by serial dilution of the stock solutions in cell culture medium to provide final concentrations of 0.006–100 μM.

All tumor lines were propagated under sterile conditions and incubated at 37° C. in HEPA-filtered $CO_2$ tissue culture incubators with 5% $CO_2$ and 95% humidity in colorless RPMI 1640 medium (Mediatech, Hemdon, Va.) containing 5% fetal bovine serum (complete medium). The ovarian and colon tumor cell lines were plated in microtiter plates at a density of 5,000 cells per well. The lung lines were plated at a density of 10,000 cells per well.

Viable cell number was measured by the MTS dye conversion assay after a total of 72 hours of treatment. Sample wells were treated with 20 μl of the MTS solution warmed to 37° C. The plates were incubated for four hours at 37 20 C. The absorbance was measured at 490 nm on a Coulter microplate reader.

Drug potency was expressed by $GI_{50}$ values and calculated by a non-linear regression analysis of the values above and below 50% of the control. The results are summarized in Table 2 below.

TABLE 2

Growth Inhibition ($GI_{50}$) Values (μM)

| Platinum Compound | HT29 | HCT-116 | NCI-H69 | NCI-H69/AR | A2780 | A2780/DDPT |
|---|---|---|---|---|---|---|
| Cisplatin | 61 | 43 | 15 | 15 | 15 | 57 |
| CDTA-di-platinum | 78 | 24 | 6.69 | 8.9 | 5.45 | 49 |
| CDTA-mono-platinum | 65 | 38 | 10 | 18 | 5.57 | 50 |

As shown in Table 2, CDTA-diplatinum and CDTA-monoplatinum show potency comparable to or greater than cisplatin in all cell lines.

Example 8

Effect of pH on CDTA-Diplatinum/CDTA-Monoplatinum Interconversion

Cyclohexane-trans-1,2-diaminetetraacetic-acid-diplatinum (CDTA-diplatinum) was prepared according to Example 1. Three solutions of CDTA-diplatinum were prepared: 1 mg/ml in water (pH ~6.5) (Solution 1); 1 mg/ml in 0.01 N NaOH (pH~9.5) (Solution 2); and 1 mg/ml in 0.01 N HCl (pH~2) (Solution 3). The percentage ratio of CDTA-diplatinum/CDTA-monoplatinum was determined using HPLC. The results are as follows: Solution 1, 54% CDTA-diplatinum and 45% CDTA-monoplatinum; Solution 2, 1% CDTA-diplatinum and 99% CDTA-monoplatinum; and Solution 3, 2% CDTA-diplatinum and 98% CDTA-monoplatinum. A schematic illustration of the interconversion of cyclohexane-trans-1,2-diaminetetraacetic-acid-diplatinum and cyclohexane-trans-1,2-diaminetetraacetic-acid-monoplatinum is illustrated in FIG. 1.

While the preferred embodiment of the invention has been illustrated and described, it will be appreciated that various changes can be made therein without departing from the spirit and scope of the invention.

The invention claimed is:

1. A compound having the formula wherein $X_1$ and $X_2$ are independently selected from the group consisting of ammonia, amino, nitro, C1–C6 alkoxy, hydroxy, chloride, bromide, and iodide;

wherein $Y_1$ and $Y_2$ are independently selected from the group consisting of a direct bond from the cycloalkane ring to the nitrogen atom and a C1–C6 straight chain or branched alkyl group;

wherein $Z_1$ is $C(R_1)R_2$, wherein $R_1$ and $R_2$ are independently hydrogen or C1–C6 straight chain or branched alkyl;

wherein $Z_2$ is $C(R_3)R_4$, wherein $R_3$ and $R_4$ are independently hydrogen or C1–C6 straight chain or branched alkyl; and wherein m=0, 1, 2, 3, 4, or 5, n=0, 1, 2, 3, 4, or 5, provided that m+n≧2 and m+n≦5.

2. The compound of claim 1, wherein $X_1$ and $X_2$ are independently selected from ammonia and hydroxy.

3. The compound of claim 1, wherein $Y_1$ and $Y_2$ are direct bonds.

4. The compound of claim 1, wherein m=0 and n=4.

5. The compound of claim 1, wherein $X_1$ and $X_2$ are ammonia, $Y_1$ and $Y_2$ are direct bonds, m=0, n=4, and $R_1$, $R_2$, $R_3$ and $R_4$ are hydrogen.

6. A compound having the formula wherein M is selected from the group consisting of hydrogen and a metal ion;

wherein $Y_1$ and $Y_2$ are the same and are selected from the group consisting of a direct bond from the cycloalkane ring to the nitrogen atom and —$CH_2$—; and wherein n=0, 1, 2, or 3.

7. The compound of claim 6, wherein M is hydrogen.

8. The compound of claim 6, wherein $Y_1$ and $Y_2$ are direct bonds.

9. The compound of claim 6, wherein n=2.

10. The compound of claim 6, wherein M is hydrogen, $Y_1$ and $Y_2$ are direct bonds, and n=2.

11. A compound having the formula wherein $X_1$, $X_2$, $X_3$, and $X_4$ are independently selected from the group consisting of nitro, C1–C6 alkoxy, hydroxy, chloride, bromide, and iodide;
wherein $Z_1$ is $C(R_1)R_2$, wherein $R_1$ and $R_2$ are independently hydrogen or C1–C6 straight chain or branched alkyl;
wherein $Z_2$ is $C(R_3)R_4$, wherein $R_3$ and $R_4$ are independently hydrogen or C1–C6 straight chain or branched alkyl; and
wherein m=0, 1, 2, or 3, n=0, 1, 2, or 3, provided that m+n≧0 and m+n≦3.

12. The compound of claim 11, wherein $X_1$, $X_2$, $X_3$, and $X_4$ are hydroxy.

13. A compound having the formula wherein M is selected from the group consisting of hydrogen and a metal ion;
wherein $X_1$ and $X_2$ are independently selected from the group consisting of ammonia, amino, nitro, C1–C6 alkoxy, hydroxy, chloride, bromide, and iodide;
wherein $Z_1$ is $C(R_1)R_2$, wherein $R_1$ and $R_2$ are independently hydrogen or C1–C6 straight chain or branched alkyl;
wherein $Z_2$ is $C(R_3)R_4$, wherein $R_3$ and $R_4$ are independently hydrogen or C1–C6 straight chain or branched alkyl; and
wherein m=0, 1, 2, or 3, n=0, 1, 2, or 3, provided that m+n≧0 and m+n≦3.

14. A pharmaceutical composition, comprising a compound of claim 1 and a pharmaceutically acceptable carrier.

15. The composition of claim 14 further comprising a second anticancer agent.

16. A method for treating a cellular proliferative disease, comprising administering a therapeutically effective amount of a compound of claim 1 to a subject in need thereof.

17. The method of claim 16, wherein the cellular proliferative disease is a hematologic cancer.

18. The method of claim 16, wherein the cellular proliferative disease is a nonhematologic cancer.

19. A pharmaceutical composition, comprising a compound of Claim 6 and a pharmaceutically acceptable carrier.

20. The composition of Claim 19 further comprising a second anticancer agent.

21. A method for treating a cellular proliferative disease, comprising administering a therapeutically effective amount of a compound of Claim 6 to a subject in need thereof.

22. The method of Claim 21, wherein the cellular proliferative disease is a hematologic cancer.

23. The method of Claim 21, wherein the cellular proliferative disease is a nonhematologic cancer.

* * * * *

UNITED STATES PATENT AND TRADEMARK OFFICE
CERTIFICATE OF CORRECTION

PATENT NO. : 7,129,368 B2
APPLICATION NO. : 11/080348
DATED : October 31, 2006
INVENTOR(S) : M. Lal It is certified that error appears in the above-identified patent and that said Letters Patent is hereby corrected as shown below:

| COLUMN | LINE | ERROR |
|---|---|---|
| (56) Pg. 1, col. 2 | Refs. Cited (Other Publs., Item 1) | "Potentail" should read --Potential-- |
| (56) Pg. 2, col. 1 | Refs. Cited (Other Publs., Item 4) | "*Cinical*" should read --*Clinical*-- |
| (56) Pg. 2, col. 1 | Refs. Cited (Other Publs., Item 5) | "*Inorgica*" should read --*Inorganica*-- |
| 21 (Claim 11, | 28 line 12 of text) | "m+n$\geq$0and" should read --m+n$\geq$0 and-- |
| 22 (Claim 13, | 15 line 14 of text) | "m+n$\geq$0and" should read --m+n$\geq$0 and-- |

Signed and Sealed this

Twentieth Day of March, 2007

JON W. DUDAS
*Director of the United States Patent and Trademark Office*